United States Patent
Onishi et al.

(10) Patent No.: US 12,193,648 B2
(45) Date of Patent: Jan. 14, 2025

(54) LIQUID FEEDING CONDUIT AND ENDOSCOPE REPROCESSOR

(71) Applicant: OLYMPUS MEDICAL SYSTEMS CORP., Tokyo (JP)

(72) Inventors: Hideto Onishi, Hachioji (JP); Kazuya Mitsueda, Hino (JP); Takumi Tsuzuki, Kawasaki (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 774 days.

(21) Appl. No.: 17/232,536

(22) Filed: Apr. 16, 2021

(65) Prior Publication Data

US 2022/0330801 A1 Oct. 20, 2022

(51) Int. Cl.
*A61B 1/12* (2006.01)
*A61B 1/015* (2006.01)

(52) U.S. Cl.
CPC .............. *A61B 1/123* (2013.01); *A61B 1/125* (2013.01); *A61B 1/015* (2013.01)

(58) Field of Classification Search
CPC ................................ A61B 1/123; A61B 1/125
See application file for complete search history.

(56) References Cited

U.S. PATENT DOCUMENTS

| | | | | |
|---|---|---|---|---|
| 5,551,462 A * | 9/1996 | Biermaier | ............... | A61B 1/123 134/169 C |
| 8,298,494 B2 * | 10/2012 | Komiya | ................ | A61B 1/125 422/292 |
| 9,505,038 B2 * | 11/2016 | Iwasaki | ................... | A61B 1/123 |
| 9,629,519 B2 * | 4/2017 | Takazawa | ............... | B08B 9/032 |
| 11,000,863 B2 * | 5/2021 | Wiyninger | ............ | B05B 15/555 |
| 2007/0089487 A1 * | 4/2007 | Jackson | ..................... | A61L 2/24 73/37 |
| 2007/0193605 A1 * | 8/2007 | Kuroshima | ............... | A61L 2/24 134/166 R |
| 2009/0205687 A1 * | 8/2009 | Onishi | .................. | F16L 37/127 134/136 |
| 2017/0055942 A1 * | 3/2017 | Tsuruta | ................... | F16K 31/00 |

FOREIGN PATENT DOCUMENTS

| | | |
|---|---|---|
| JP | 2009-195400 A | 9/2009 |
| JP | 5220435 B2 | 6/2013 |

* cited by examiner

*Primary Examiner* — John P Leubecker
(74) *Attorney, Agent, or Firm* — Scully, Scott, Murphy & Presser, P.C.

(57) ABSTRACT

A liquid feeding conduit includes: a tube body of a cleaning tube through which a fluid passes; an endoscope-side connector provided at an end of the tube body, the endoscope-side connector being connected to a conduit cap of an endoscope conduit; a valve element provided in the endoscope-side connector, the valve element being configured to move toward a side of the conduit cap by a supply pressure of the fluid to thereby watertightly connect the endoscope-side connector and the conduit cap; a spring configured to bias the valve element toward an opposite side of the conduit cap; and a buffer unit configured to delay the movement of the valve element toward the side of the conduit cap.

11 Claims, 16 Drawing Sheets

LIQUID FEEDING CONDUIT AND ENDOSCOPE REPROCESSOR

BACKGROUND OF THE INVENTION

1. Field of the Invention

The present invention relates to a liquid feeding conduit that feeds a cleaning liquid into a channel at a time of cleaning and disinfecting an endoscope, and to an endoscope reprocessor.

2. Description of the Related Art

In recent years, endoscopes have been widely used in a medical field and an industrial field. Endoscopes used in the medical field can allow observation of an organ in a body cavity by inserting an elongated insertion portion into the body cavity, or allow various treatments by using treatment instruments inserted into a treatment instrument insertion channel of an endoscope when necessary.

Endoscopes used in the medical field are used in a state of being inserted into a body cavity particularly for an inspection and treatment and hence, after an endoscope is used, it is necessary to clean and disinfect the endoscope to use the endoscope again. It is well known that a used endoscope is cleaned and disinfected by an endoscope cleaning and disinfecting device, which is an endoscope reprocessor, for example.

There is a known configuration of an endoscope cleaning and disinfecting device of this kind, where an endoscope-side connector of a cleaning tube is connected to a cap of an endoscope conduit, such as a treatment instrument insertion channel, formed in the endoscope, and any of various medicinal solutions is supplied to the endoscope conduit through the cleaning tube to clean and disinfect also the endoscope conduit.

For example, Japanese Patent No. 5220435 also discloses a technique where when supply of any of various medicinal solutions is started, leakage is intentionally caused between a cap and an endoscope-side connector to clean and disinfect also the cap with the any of various medicinal solutions.

SUMMARY OF THE INVENTION

One aspect of the present invention is directed to a liquid feeding conduit that supplies a fluid to an endoscope conduit of an endoscope disposed in an endoscope reprocessor, the liquid feeding conduit including: a tube body through which the fluid passes; a connector provided at an end of the tube body, the connector being configured to be attached to and detached from a cap of the endoscope conduit; a valve provided in the connector, the valve being configured to move toward a side of the cap by a supply pressure of the fluid to thereby watertightly connect the connector and the cap; a biasing member configured to bias the valve toward an opposite side of the cap; and a buffer mechanism configured to delay the movement of the valve toward the side of the cap.

Another aspect of the present invention is directed to an endoscope reprocessor including a liquid feeding conduit that supplies a fluid to an endoscope conduit of an endoscope, the liquid feeding conduit including: a tube body through which the fluid passes; a connector provided at an end of the tube body, the connector being configured to be attached to and detached from a cap of the endoscope conduit; a valve provided in the connector, the valve being configured to move toward a side of the cap by a supply pressure of the fluid to thereby watertightly connect the connector and the cap; a biasing member configured to bias the valve toward an opposite side of the cap; and a buffer mechanism configured to delay the movement of the valve toward the side of the cap.

DETAILED DESCRIPTION OF THE PREFERRED EMBODIMENTS

Figure 1:
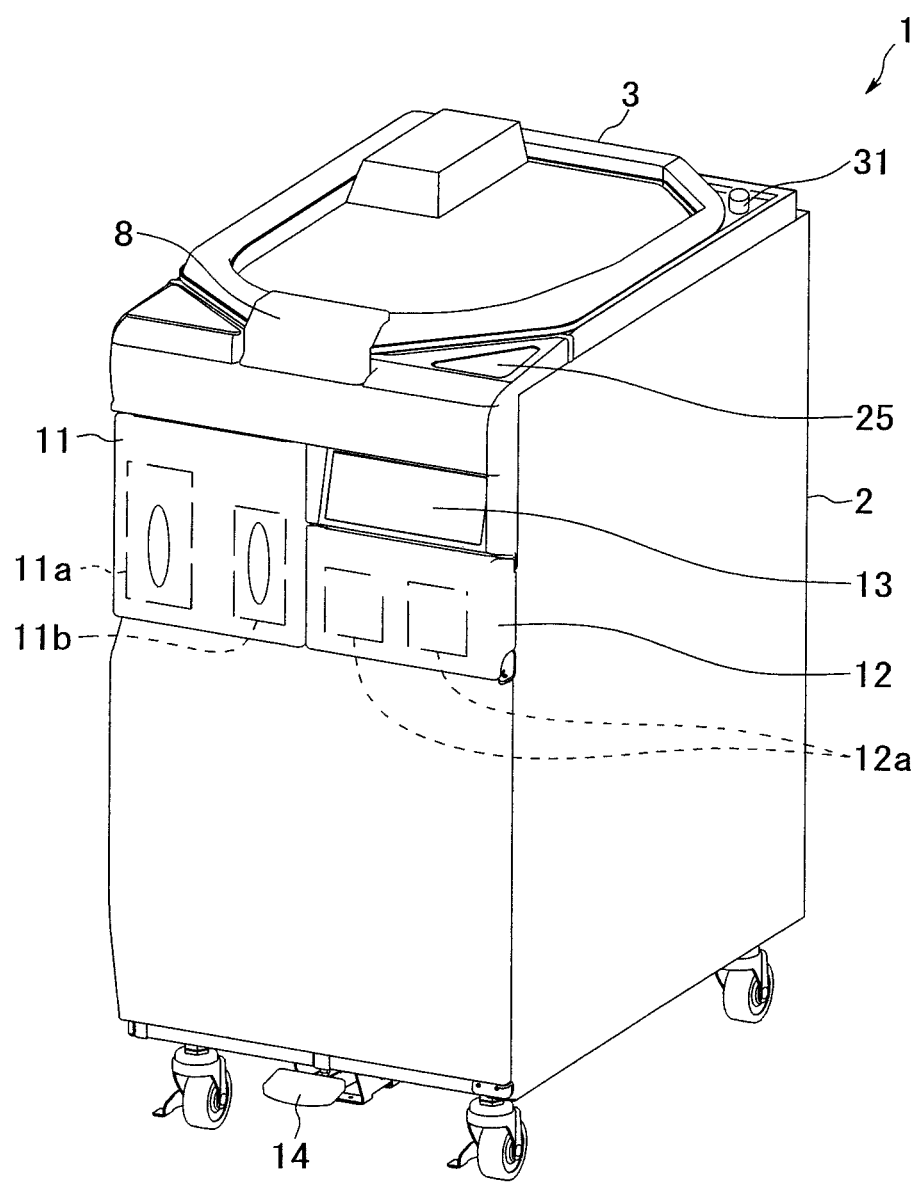
FIG. 1 is a perspective view of an endoscope cleaning and disinfecting device according to a first embodiment.
Figure 2:
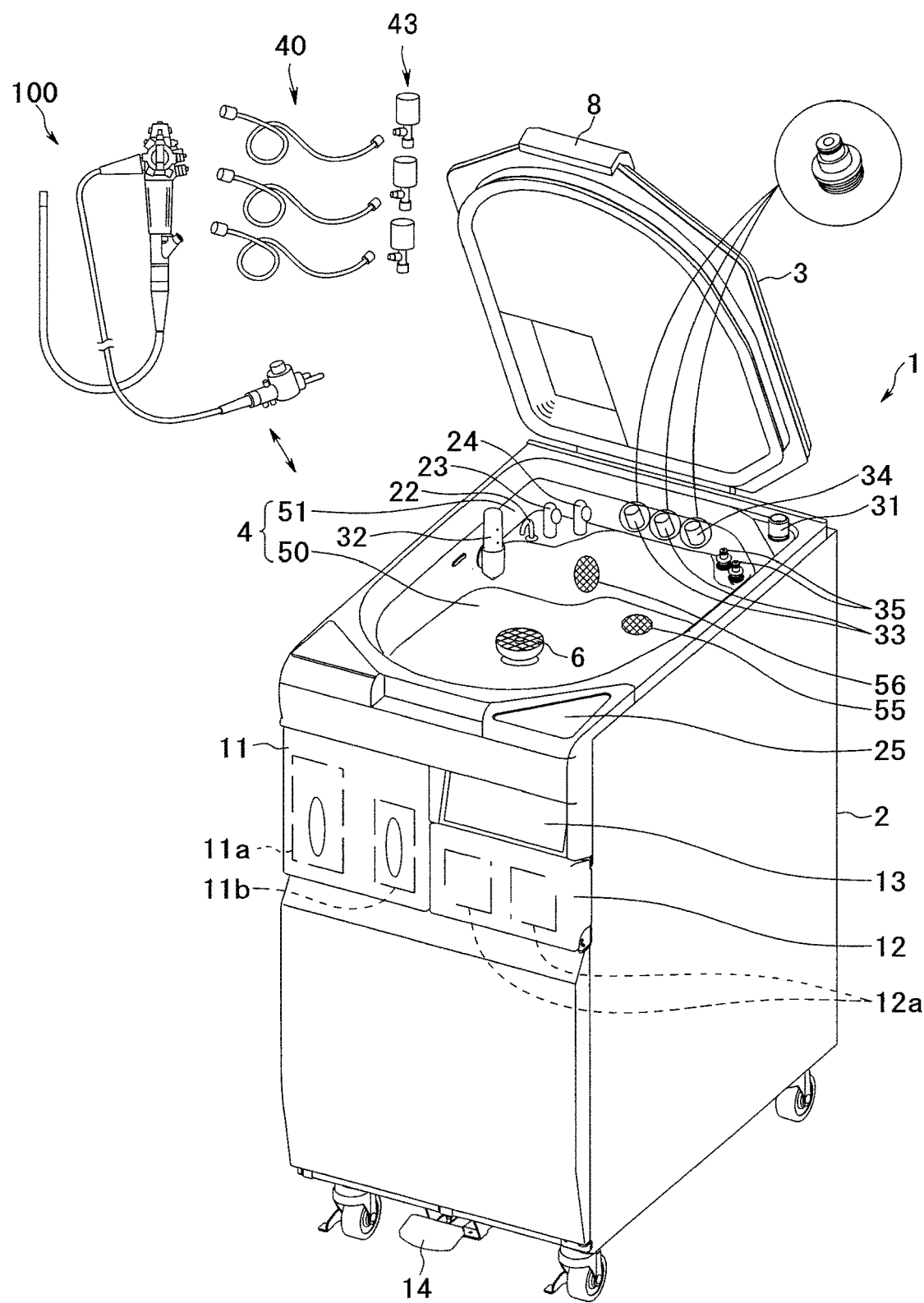
FIG. 2 is a perspective view of the endoscope cleaning and disinfecting device according to the first embodiment showing a state in which a top cover is opened, so that an endoscope can be accommodated in a cleaning and disinfecting tank.

Hereinafter, embodiments of the present invention will be described with reference to drawings. Drawings relate to one embodiment of the present invention. FIG. 1 is a perspective view of an endoscope cleaning and disinfecting device. FIG. 2 is a perspective view of the endoscope cleaning and disinfecting device showing a state in which a top cover shown in FIG. 1 is opened, so that an endoscope can be accommodated in a cleaning and disinfecting tank.

As shown in FIG. 1 and FIG. 2, an endoscope cleaning and disinfecting device 1, which is an endoscope reprocessor, is a device for cleaning and disinfecting a used endoscope 100. The endoscope cleaning and disinfecting device 1 is configured to include a device body 2 having a cleaning and disinfecting tank 4 at an upper portion, and a top cover 3, which is a lid body capable of opening and closing the cleaning and disinfecting tank 4.

The top cover 3 is coupled with the device body 2 in a swingable manner. In other words, a fixed end side of the top cover 3 is connected to a back side of the upper portion of the device body 2 in a swingable manner via hinges not shown in the drawing, for example.

Further, a free end side of the top cover 3 is provided with a latch 8 that can be engaged with a front side of the upper portion of the device body 2. The latch 8 is configured such that the latch 8 can be engaged with the device body 2 when the top cover 3 closes the cleaning and disinfecting tank 4. With such engagement of the latch 8, it is possible to maintain a closed state of the cleaning and disinfecting tank 4 brought about by the top cover 3 (see FIG. 1).

The latch 8 is also configured such that the engagement of the latch 8 with the device body 2 is released with a depressing operation of a pedal switch 14 provided at a lower portion of the device body 2, for example. With such release of the engagement of the latch 8, the cleaning and disinfecting tank 4 closed by the top cover 3 can be opened (see FIG. 2).

A detergent/alcohol tray 11 is disposed at an upper portion of a left half portion of a front surface of the device body 2, for example.

A detergent tank 11a and an alcohol tank 11b are held by the detergent/alcohol tray 11. The detergent tank 11a stores a cleaning agent, which is a fluid (liquid) used in cleaning the endoscope 100. The alcohol tank 11b stores alcohol, which is a fluid (liquid) used in drying the cleaned and disinfected endoscope 100. Cleaning agent and alcohol can be appropriately refilled into the detergent tank 11a and the alcohol tank 11b by withdrawing the detergent/alcohol tray 11 frontward from the device body 2.

In the present embodiment, the cleaning agent is a concentrated detergent diluted to a predetermined concentration with tap water on which sterilizing treatment is applied by a feed water filter. In the present embodiment, in the description made hereinafter, a mixed liquid of the cleaning agent and the tap water is referred to as "cleaning liquid".

A cassette tray 12 is also disposed at an upper portion of a right half portion of the front surface of the device body 2, for example.

Medicinal solution bottles 12a are held by the cassette tray 12. An undiluted solution of a disinfecting liquid, such as peracetic acid, is injected into the medicinal solution bottle 12a as a fluid (liquid) used in disinfecting the endoscope 100. The medicinal solution bottle 12a can be suitably replaced by withdrawing the cassette tray 12.

A sub-operation panel 13 is disposed above the cassette tray 12 on the front surface of the device body 2. A cleaning and disinfecting time period is displayed on the sub-operation panel 13, and instruction buttons and the like for heating a disinfecting liquid are disposed on the sub-operation panel 13.

As shown in FIG. 2, a main operation panel 25 is provided to an upper surface of the device body 2 at a position laterally adjacent to a front portion of the cleaning and disinfecting tank 4, for example. The main operation panel 25 is provided with setting switches, such as a switch for starting a cleaning and disinfecting action of the device body 2 and a switch for selecting a cleaning and disinfecting mode.

A water supply hose connection portion 31 is provided to the upper surface of the device body 2 at a position laterally adjacent to a rear portion of the cleaning and disinfecting tank 4, for example. A hose connected to a water faucet is connected to the water supply hose connection portion 31. Tap water is supplied from the water faucet to the device body 2 via the water supply hose connection portion 31.

The cleaning and disinfecting tank 4 is configured to include a tank body 50, and a terrace portion 51 formed at a position higher than the tank body 50.

The tank body 50 has a recessed portion that can accommodate the used endoscope 100 which is to be cleaned and disinfected. A bottom surface of the tank body 50 has a drainage port 55 for draining a fluid (liquid), such as a cleaning liquid, water, alcohol, or a disinfecting liquid.

A side surface of the tank body 50 has a circulation port 56 at a desired position. The circulation port 56 takes in a portion of a fluid (liquid), such as a cleaning liquid, water, alcohol, or a disinfecting liquid, supplied to the tank body 50. The liquid taken into the circulation port 56 can be supplied to respective conduits (endoscope conduits 103), which are disposed in the endoscope 100, via cleaning tubes 40 described later. Alternatively, the liquid taken into the circulation port 56 can be supplied to the tank body 50 again from a liquid supply circulation nozzle 24 described later.

A cleaning case 6 is disposed at a substantially center portion of the bottom surface of the tank body 50. The cleaning case 6 is provided for accommodating various components removable from the endoscope 100 so as to clean and disinfect the various components together with the endoscope 100.

A cover-equipped liquid level sensor 32 is provided at a desired position on the side surface of the tank body 50. The cover-equipped liquid level sensor 32 detects a liquid level of a cleaning liquid, water, alcohol, a disinfecting liquid or the like supplied to the tank body 50.

The terrace portion 51 is provided with a detergent nozzle 22, a disinfecting liquid nozzle 23, and the liquid supply circulation nozzle 24. The detergent nozzle 22 supplies a cleaning agent from the detergent tank 11a to the tank body 50, the cleaning agent having been diluted to a predetermined concentration with tap water. The disinfecting liquid nozzle 23 supplies a disinfecting liquid from the medicinal solution bottle 12a to the tank body 50, the disinfecting liquid having been diluted in a disinfecting liquid tank not shown in the drawing. The liquid supply circulation nozzle 24 supplies alcohol from the alcohol tank 11b, or a fluid, such as a cleaning liquid, water, alcohol, or a disinfecting liquid, taken into the circulation port 56 of the tank body 50 to the tank body 50.

The terrace portion 51 is also provided with two air feeding water feeding/forceps ports 33, a forceps raising port 34, and two water leakage detection ports 35, for example.

The air feeding water feeding/forceps ports 33 and the forceps raising port 34 can supply a fluid, such as a cleaning liquid, water, alcohol, a disinfecting liquid, or air, to channels being the endoscope conduits 103 provided in the endoscope 100, for example. Therefore, in the device body 2, for example, an alcohol conduit 17, a circulation conduit 18, and an air feeding conduit 19 are connected to the air feeding water feeding/forceps ports 33 and the forceps raising port 34.

Figure 7:
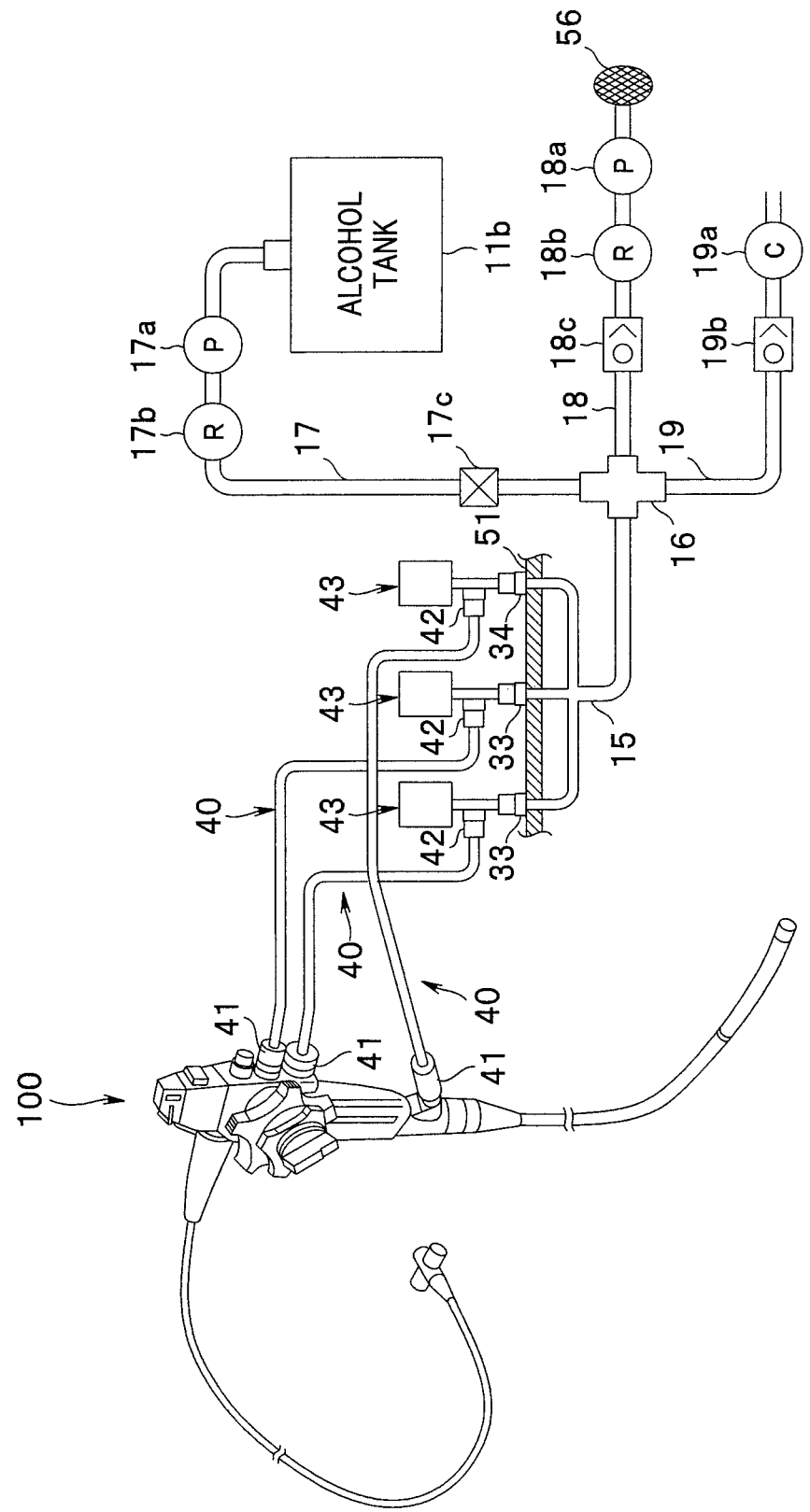
FIG. 7 is a schematic view showing a liquid feeding conduit connected to the endoscope, according to the first embodiment.

More specifically, for example, as shown in FIG. 7, three branch ends of a channel conduit 15 are respectively connected to the air feeding water feeding/forceps ports 33 and the forceps raising port 34. One end side of the alcohol conduit 17, one end side of the circulation conduit 18, and one end side of the air feeding conduit 19 are connected to an assembled end of the channel conduit 15 via a channel block 16.

The alcohol tank 11b is connected to the other end side of the alcohol conduit 17. A hydraulic pump 17a, a regulator 17b, and a solenoid valve 17c are provided to intermediate portions of the alcohol conduit 17. The hydraulic pump 17a is provided for force-feeding alcohol in the alcohol tank 11b. The regulator 17b is provided for regulating pressure of liquid (alcohol) discharged from the hydraulic pump 17a to a regulator pressure, which is a supply pressure set in advance. The solenoid valve 17c is provided for opening and closing an intermediate portion of the alcohol conduit 17.

The other end side of the circulation conduit 18 is connected to the circulation port 56 formed on the tank body 50 of the cleaning and disinfecting tank 4. A hydraulic pump 18a, a regulator 18b, and a check valve 18c are provided to intermediate portions of the circulation conduit 18. The hydraulic pump 18a is provided for force-feeding a liquid, such as a cleaning liquid, water, alcohol, or a disinfecting liquid, taken into the circulation port 56. The regulator 18b is provided for regulating pressure of liquid discharged from the hydraulic pump 18a to the regulator pressure, which is a supply pressure set in advance. The check valve 18c is provided for inhibiting allow of a fluid from one end side to the other end side of the circulation conduit 18.

A compressor 19a and a check valve 19b are provided to intermediate portions of the air feeding conduit 19. The compressor 19a is provided for force-feeding air taken into the device body 2 from the outside. The check valve 19b is provided for inhibiting a flow of a fluid from one end side to the other end side of the air feeding conduit 19.

The hydraulic pump 17a, the regulator 17b, the solenoid valve 17c, the hydraulic pump 18a, the regulator 18b, the compressor 19a and the like are controlled by a well-known control unit provided with a CPU, a RAM, a ROM, a nonvolatile storage unit and the like. With such control, a fluid, such as a cleaning liquid, water, alcohol, a disinfecting liquid, or air, is selectively supplied to each of the air feeding water feeding/forceps ports 33 and the forceps raising port 34.

A device-side connector 42, which is a connector provided to one end of the cleaning tube 40, is mounted on each of the air feeding water feeding/forceps ports 33 and the forceps raising port 34 via a buffer unit 43, which is a buffer mechanism, for example. With such a configuration, a liquid feeding conduit is formed in the endoscope cleaning and disinfecting device 1, the liquid feeding conduit including the cleaning tube 40, the buffer unit 43, the channel conduit 15 and the like.

Figure 3:
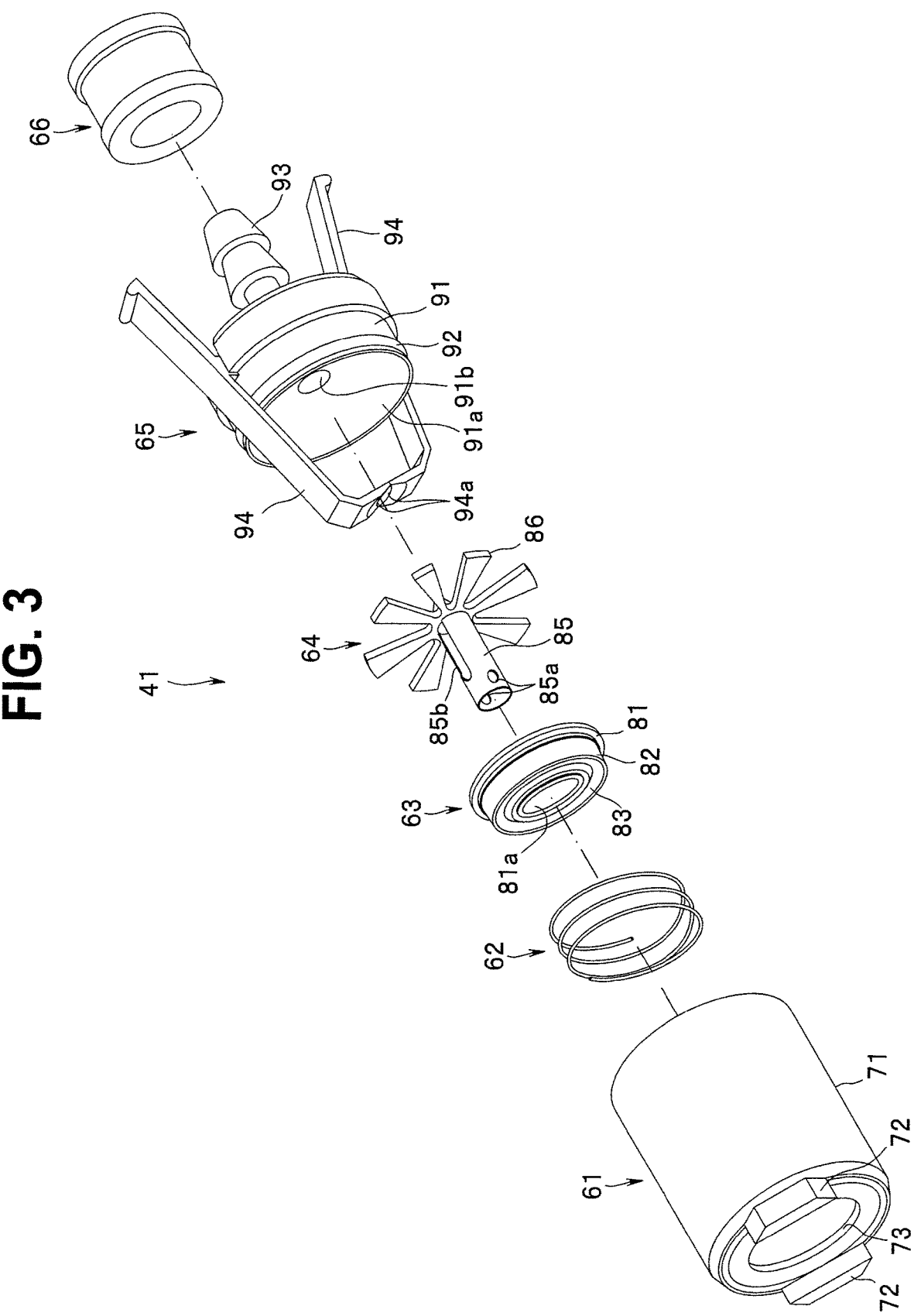
FIG. 3 is an exploded perspective view showing an endoscope-side connector of a cleaning tube according to the first embodiment.
Figure 4:
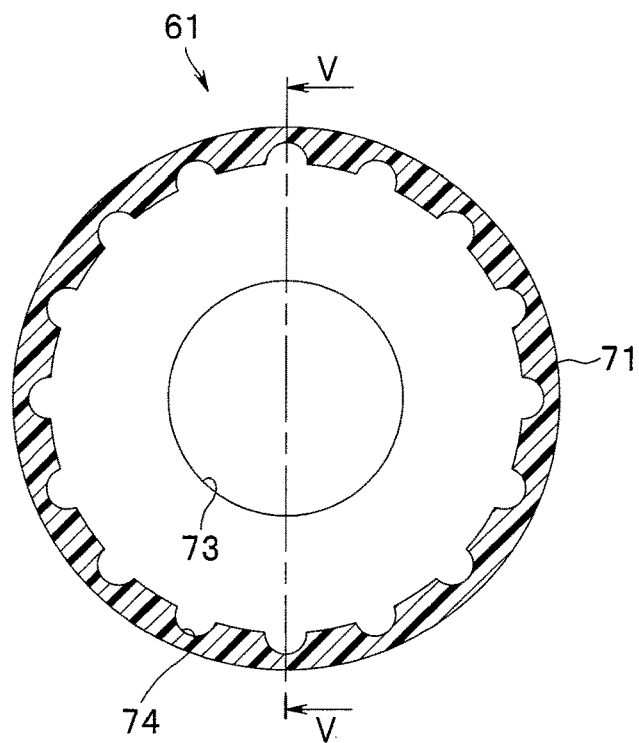
FIG. 4 is a cross-sectional view of a connector case according to the first embodiment.
Figure 5:
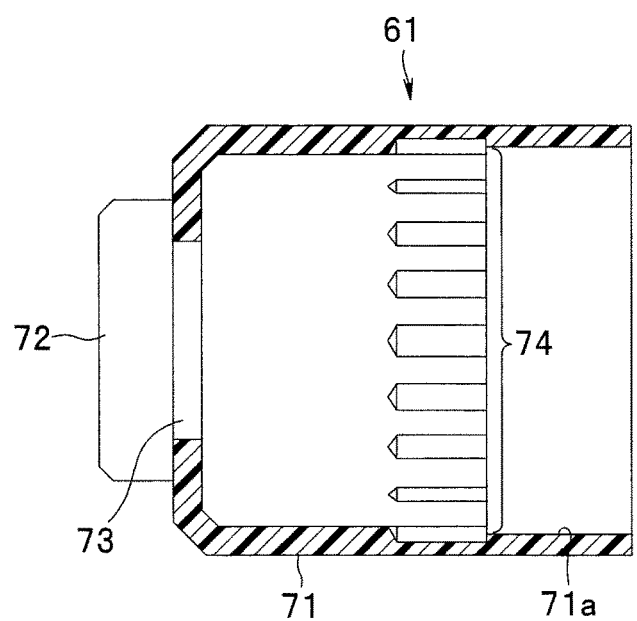
FIG. 5 is a cross-sectional view of the connector case according to the first embodiment taken along line V-V in FIG. 4.
Figure 6:
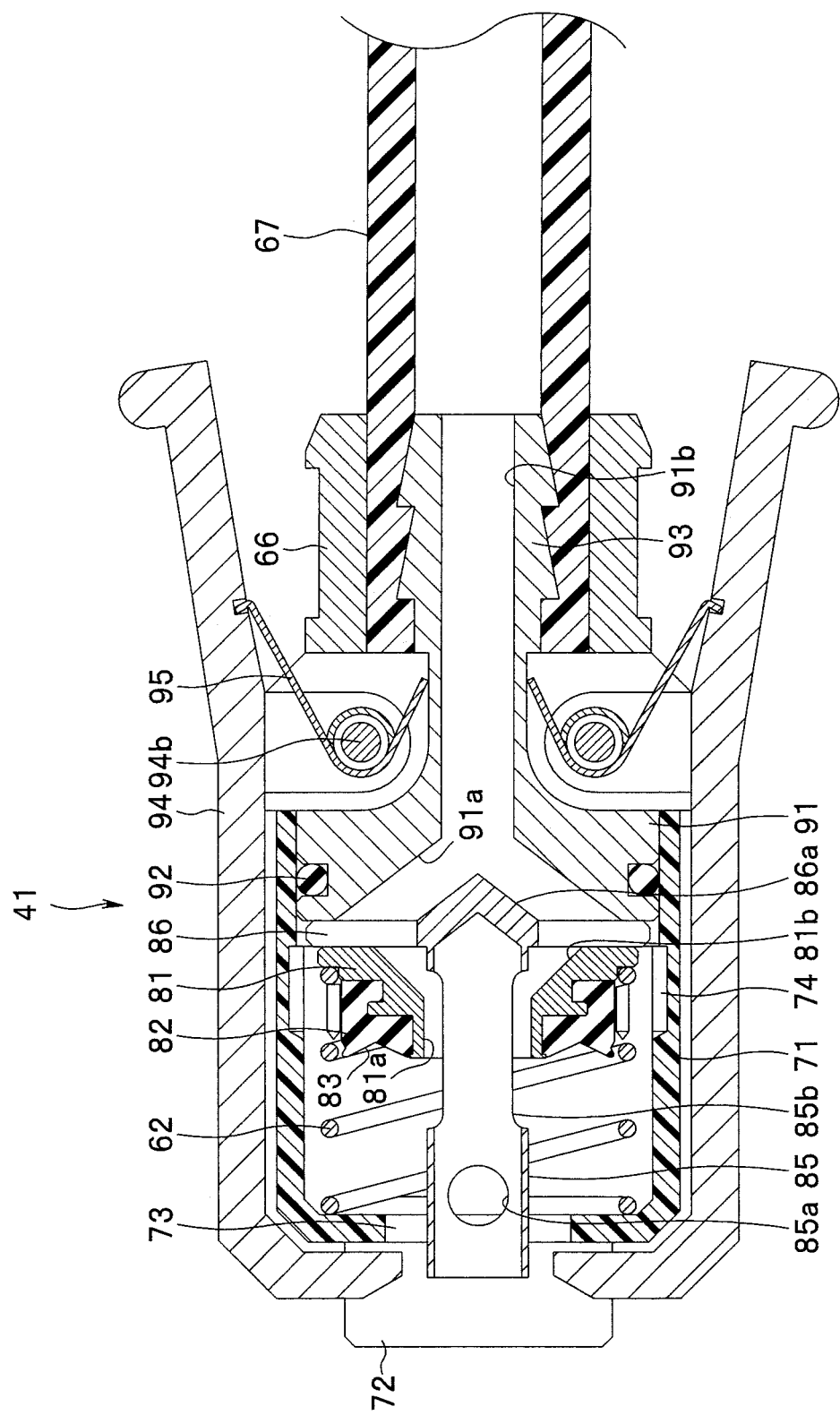
FIG. 6 is a cross-sectional view showing the endoscope-side connector of the cleaning tube according to the first embodiment.

Further, an endoscope-side connector 41 (see FIG. 3), which is a connector portion in the present embodiment disposed at the other end of the cleaning tube 40, is mounted on a conduit cap, which is the cap of the endoscope conduit 103 of the endoscope 100.

Next, the endoscope-side connector 41 of the cleaning tube 40 will be described in detail hereinafter with reference to FIG. 3 to FIG. 6. In the description made hereinafter, the description will be made assuming that the side of the endoscope-side connector 41 connected to the conduit cap, which is a channel connector portion of the endoscope 100, is a front side.

The endoscope-side connector 41 is configured to include a substantially cylindrical connector case 61, a spring 62 serving as a biasing member, a valve element 63 serving as an annular valve, a blade-equipped pipe body 64, a sealing pipe body 65, and a fixing pipe 66.

The connector case 61 includes two protruding portions 72 extending from a front surface of a case body 71. The protruding portions 72 are disposed to face each other across an opening portion 73 formed in the front surface of the case body 71. The case body 71 also has a plurality of recessed portions 74 arranged on an inner peripheral surface in a circumferential direction of the inner peripheral surface. The respective recessed portions 74 are formed to extend in a longitudinal direction (center axis direction) of the case body 71. The case body 71 also has a stepped portion 71a therein to increase an inner diameter of the case body 71 at a position rearward of the recessed portions 74 (see FIG. 5).

The spring 62 is an elastic member for biasing the valve element 63 rearward in the case body 71.

The valve element 63 is configured to include a rigid annular portion 81 and a sealing body 82. The rigid annular portion 81 has an outward flange on a rear side. The sealing body 82 is externally fitted and mounted on the annular portion 81, the sealing body 82 being formed of an annular elastic member, such as rubber. A front surface of the sealing body 82 has an annular recessed portion 83 which recesses toward a rear side. The valve element 63 is movably accommodated to allow forward and backward motion in the case body 71 of the connector case 61, in a state in which a rearward biasing force is always applied to the valve element 63 due to the spring 62 brought into contact with the outward flange (see FIG. 6). A tapered surface 81b is formed on a proximal end side of a hole portion 81a formed in the annular portion 81 of the valve element 63, the tapered surface 81b having a conical shape reducing in diameter toward a front side. The tapered surface 81b serves as a resisting surface when a fluid flows into the hole portion 81a from a rear side toward a front side of the valve element 63. Therefore, the tapered surface 81b causes the valve element 63 to generate a force for moving the valve element 63 toward a front side against the biasing force of the spring 62 when a fluid flows toward a front side from a rear side of the endoscope-side connector 41.

The blade-equipped pipe body 64 is configured to include a cylindrical portion 85 having a substantially cylindrical shape, and a plurality of blade bodies 86 radially extending at equal intervals on a rear side of the cylindrical portion 85. The cylindrical portion 85 has two circular hole portions 85a and two elongated holes 85b, the two hole portions 85a being formed in a front portion of the cylindrical portion 85, the two elongated holes 85b being respectively formed at positions displaced from the two hole portions 85a by 90° in the circumferential direction, the two elongated holes 85b extending rearward to the blade bodies 86. When the cylindrical portion 85 of the blade-equipped pipe body 64 is accommodated in the case body 71 of the connector case 61, the cylindrical portion 85 is loosely inserted into the hole portion 81a of the annular portion 81 of the valve element 63, and is movably disposed to allow forward and backward motion with the cylindrical portion 85 protruding from the opening portion 73 of the case body 71 (see FIG. 6). The blade-equipped pipe body 64 has a tapered portion 86a at a central rear end forming a root portion of the plurality of blade bodies 86, the tapered portion 86a having a conical shape reducing in diameter toward a rear side.

When a fluid flows from the rear side toward the front side of the endoscope-side connector 41, the fluid diffused by the tapered portion 86a is pressed against the respective blade bodies 86, so that the blade-equipped pipe body 64 having such a configuration generates a force for moving the valve element 63 toward the front side against the biasing force of the spring 62.

The pressure of a fluid (regulator pressure) regulated by the above-mentioned regulators 17b, 18b is set to a pressure sufficient for moving the valve element 63 to a front end of the case body 71 against the biasing force of the spring 62. In other words, a configuration is adopted where when a fluid regulated to the regulator pressure is supplied into the endoscope-side connector 41, the tapered surface 81b of the valve element 63, the blade bodies 86 of the blade-equipped pipe body 64 and the like that receive the fluid pressure can generate a force sufficient for moving the valve element 63 to the front end of the case body 71. In other words, a configuration is adopted where when the pressure of a fluid supplied into the endoscope-side connector 41 is lower than the regulator pressure by a predetermined amount, the tapered surface 81b of the valve element 63, the blade bodies 86 of the blade-equipped pipe body 64 and the like that receive the fluid pressure cannot generate a force sufficient for moving the valve element 63 to the front end of the case body 71. Such a configuration can be achieved by comprehensively tuning the regulator pressure of a fluid, the shapes of the tapered surface 81b and the blade bodies 86, and the biasing force of the spring 62, for example.

The sealing pipe body 65 is configured to include a sealing body portion 91, an O-shaped ring 92, a tube connector portion 93, and two clip bodies 94, the sealing body portion 91 having a substantially annular shape, the O-shaped ring 92 being a sealing member fitted and mounted on an outer peripheral portion of the sealing body portion 91, the tube connector portion 93 extending from a center of a rear end side of the sealing body portion 91, the two clip bodies 94 being disposed on the outer peripheral portion of the sealing body portion 91 at positions which are point symmetrical with respect to the center of the sealing body portion 91 such that the two clip bodies 94 face each other.

The sealing body portion 91 has a tapered surface 91a having a conical shape reducing in diameter toward a rear side from a front surface. The tube connector portion 93 has a hole portion 91b which is open on a rear end side of the tube connector portion 93 with the hole portion 91b being continuously formed with the tapered surface 91a. The sealing body portion 91 is inserted into the case body 71 of the connector case 61 from a rear opening portion of the case body 71 such that the O-shaped ring 92 is brought into close contact with the above-mentioned stepped portion 71a. The sealing body portion 91 is fixed to the case body 71 by screws or the like not shown in the drawing in a state in which the sealing body portion 91 is watertightly held by the case body 71 (see FIG. 6).

A front portion of each of the two clip bodies 94 extends in a direction along a center axis of the sealing body portion 91, and a cutout portion 94a having an arc shape is formed at an extension end of the front portion. Each of the two clip bodies 94 is turnably provided to the sealing body portion 91 about a rotation axis 94b, and is biased by a torsion spring 95 in a direction along the center axis of the sealing body portion 91 (see FIG. 6). In other words, the two clip bodies 94 are biased by the torsion springs 95 about the rotation axes 94b to be closed in a direction in which the extension portions of the two clip bodies 94 on a front side come close to each other, thus being brought into contact with each other.

One end of a tube body 67 is connected to the tube connector portion 93 of the sealing body portion 91, and the fixing pipe 66 is mounted on an outer periphery of the one end of the tube body 67. The endoscope-side connector 41, to which the tube body 67 is connected, is disposed on one end of the cleaning tube 40 in this manner.

The device-side connector 42 provided at the other end of each cleaning tube 40 removably connected to the air feeding water feeding/forceps port 33 or the forceps raising port 34 is a conventional connector and hence, the detailed description of the configurations of the device-side connector 42 will be omitted.

Figure 8:
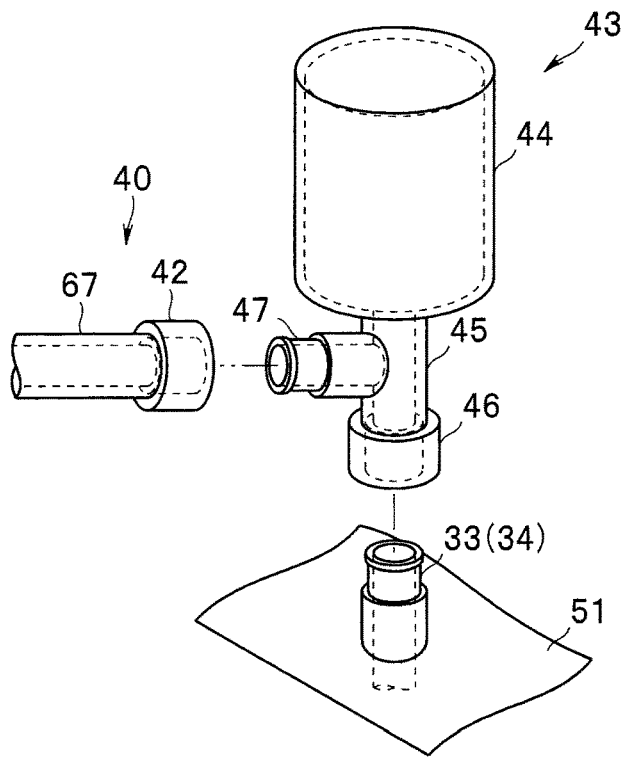
FIG. 8 is a perspective view of a buffer unit according to the first embodiment.
Figure 9:
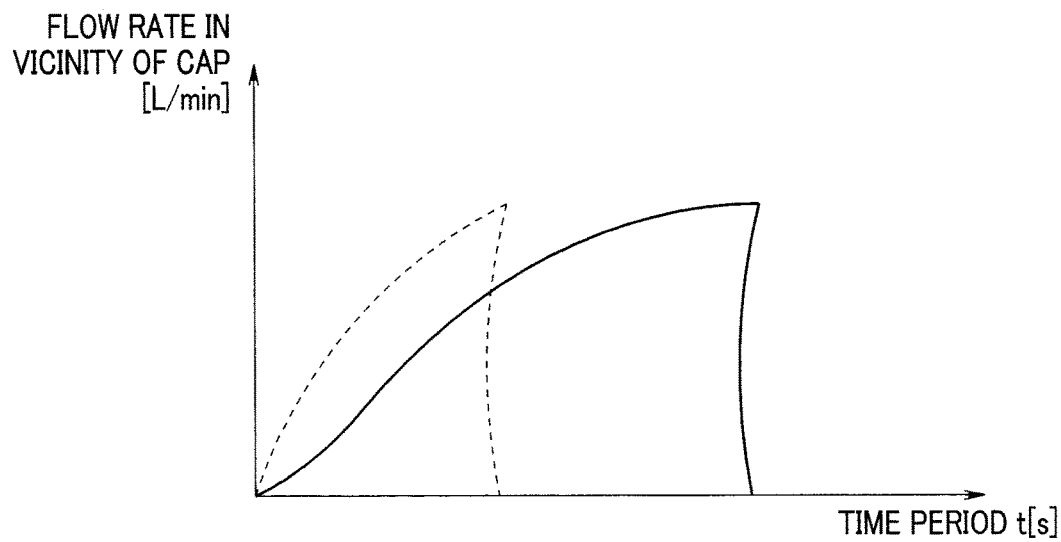
FIG. 9 is an explanatory view showing the relationship between a flow rate in a vicinity of a cap and a time period, according to the first embodiment.

Next, the buffer unit 43 will be described in detail hereinafter with reference to FIG. 7 and FIG. 8.

The buffer unit 43 has an air chamber 44 that stores air therein. A relay pipe 45 is connected to a bottom portion of the air chamber 44. More specifically, the relay pipe 45 in the present embodiment is formed of a T-shaped pipe, for example. One end side of a straight pipe portion forming the relay pipe 45 is communicated with the bottom portion of the air chamber 44.

A connector 46 is provided to the other end side of the straight pipe portion of the relay pipe 45, the connector 46 being connectable to the air feeding water feeding/forceps port 33 or the forceps raising port 34. The connector 46 has a configuration substantially equal to the configuration of the device-side connector 42 provided to the cleaning tube 40, for example.

A branch port 47 is provided to a branch pipe portion which is branched from an intermediate portion of the relay pipe 45. The branch port 47 has a configuration substantially equal to the configuration of the air feeding water feeding/ forceps ports 33 and the forceps raising port 34, for example, and is connectable to the device-side connector 42 provided to the cleaning tube 40.

The connector 46 is connected to the air feeding water feeding/forceps port 33 (or the forceps raising port 34), and the device-side connector 42 is connected to the branch port 47, so that each buffer unit 43 having such a configuration is interposed between the channel conduit 15 and the cleaning tube 40.

In such a state, the connector 46 of the buffer unit 43 is connected to the air feeding water feeding/forceps port 33 (or the forceps raising port 34) protruding from the terrace portion 51 in a substantially vertical direction, so that the air chamber 44 is disposed in a rising-up state in which the opening portion communicated with the relay pipe 45 is directed downward. The air chamber 44 is disposed as described above and hence, when a liquid is caused to flow through the relay pipe 45, air stored in the air chamber 44 is confined in the air chamber 44 without leaking to the outside in a state of receiving the pressure from the liquid.

With such a configuration, the supply pressure of the liquid supplied to the cleaning tube 40 is temporarily reduced to a pressure lower than the regulator pressure during a period from the start of the supply of the liquid to a point where the air confined in the air chamber 44 is compressed to a predetermined volume by the pressure received from the liquid.

Next, a manner of operation of the endoscope-side connector 41 of the cleaning tube 40, and the buffer unit 43 will be described in detail hereinafter with reference to FIG. 9 to FIG. 13.

Figure 10:
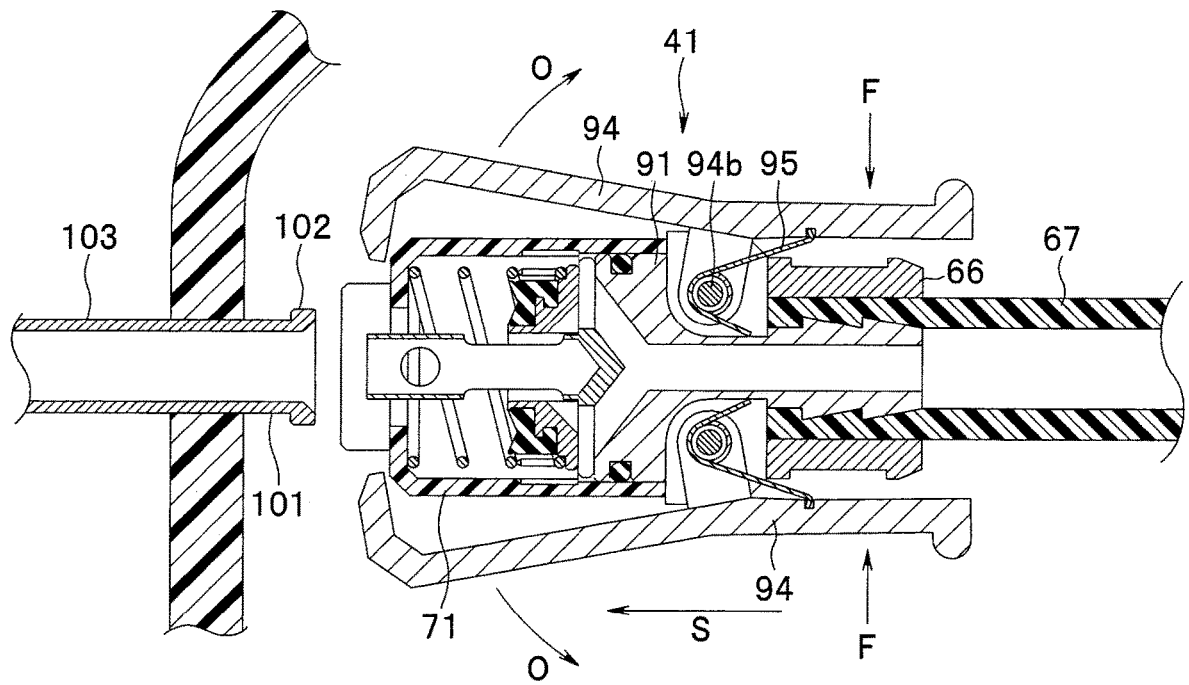
FIG. 10 is a cross-sectional view for describing a manner of operation of mounting the endoscope-side connector on a conduit cap of the endoscope, according to the first embodiment.
Figure 11:
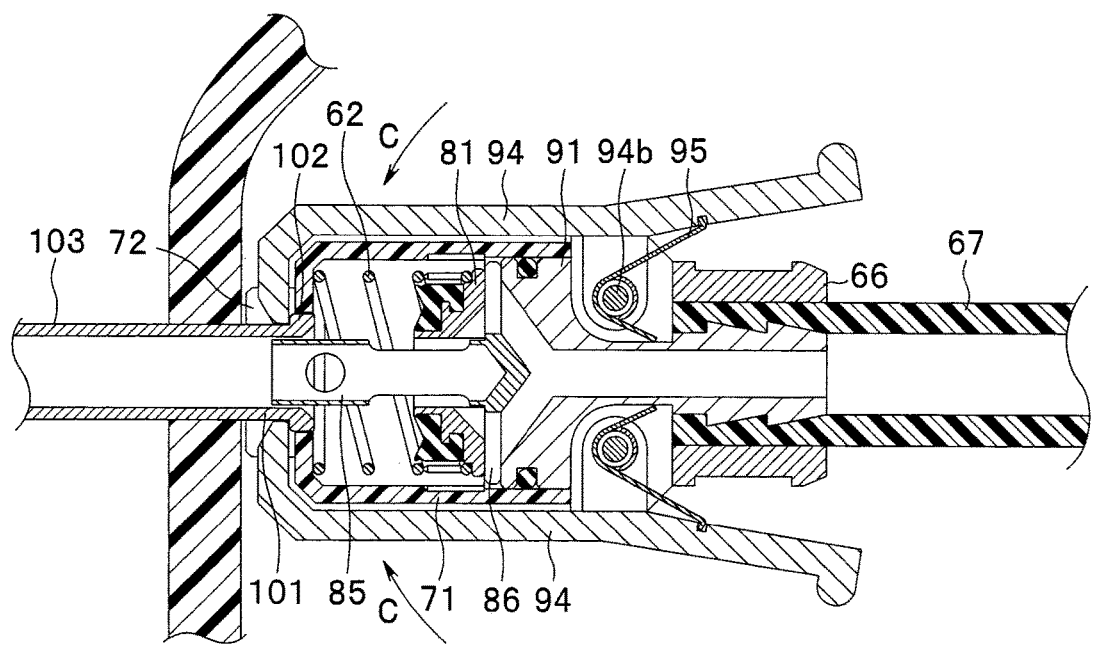
FIG. 11 is a cross-sectional view showing a state in which the endoscope-side connector is mounted on the conduit cap of the endoscope, according to the first embodiment.
Figure 12:
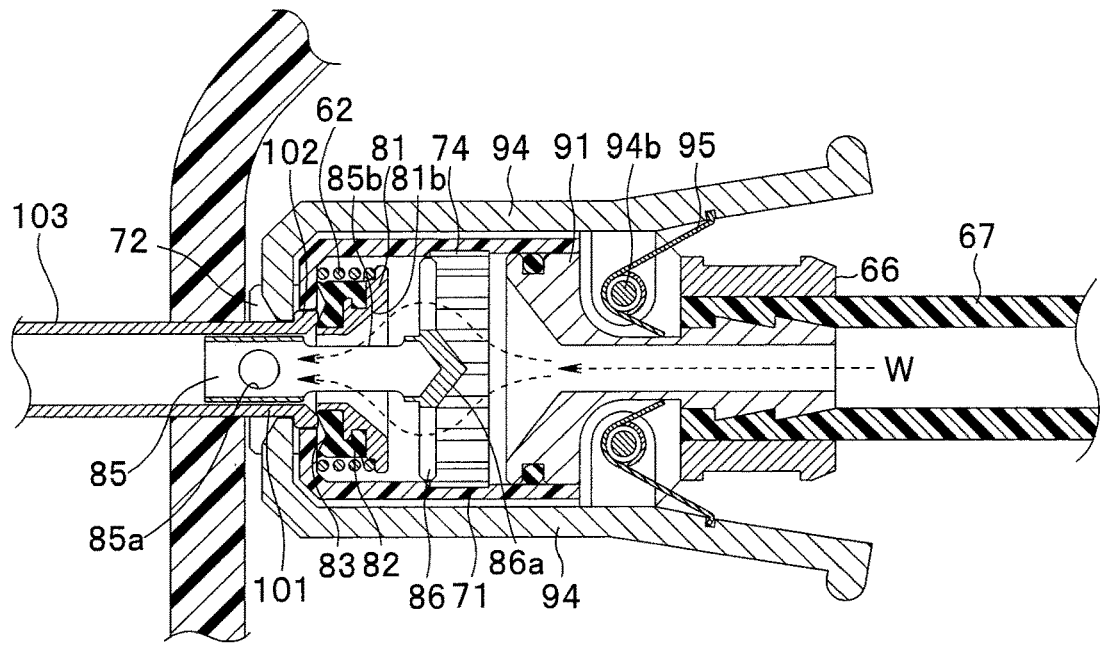
FIG. 12 is a cross-sectional view of the endoscope-side connector at a time when leakage of a fluid occurs between the endoscope-side connector and the conduit cap, according to the first embodiment.

First, as shown in FIG. 10, when the endoscope-side connector 41 of the cleaning tube 40 is connected to a conduit cap 101 of the endoscope 100, rear end portions of the clip bodies 94 are grasped. At this point of operation, the respective clip bodies 94 receive forces in directions indicated by arrows F, thus being respectively rotated in opposite directions indicated by arrows O about the rotation axes 94*b* against the biasing forces of the torsion springs 95, so that front ends of the respective clip bodies 94 are opened to be separated from each other.

The endoscope-side connector 41 is moved in a direction indicated by an arrow S toward the conduit cap 101 of the endoscope 100 while maintaining the above-mentioned state. Then, the conduit cap 101 is loosely inserted into the opening portion 73 of the case body 71 of the connector case 61, and the grasped state of the respective clip bodies 94 is released. With such operations, the respective clip bodies 94 are, by the biasing forces of the torsion springs 95, rotated about the rotation axes 94*b* in directions indicated by arrows C shown in FIG. 11, in which front end portions of the respective clip bodies 94 move toward each other, thus clamping the conduit cap 101.

At this point of operation, the cutout portions 94*a* having an arc shape (see FIG. 3) are brought into contact with an outer peripheral portion of the conduit cap 101, so that the respective clip bodies 94 fasten onto an outward flange 102 formed on the outer peripheral portion of the end side of the conduit cap 101. The endoscope-side connector 41 of the cleaning tube 40 is mounted on the conduit cap 101 of the endoscope 100 as described above.

The two protruding portions 72 provided on the front surface of the case body 71 of the connector case 61 are brought into contact with a wall surface of the endoscope 100 to prevent the conduit cap 101 from being excessively inserted into the connector case 61. The two protruding portions 72 also define a position where the respective dip bodies 94 clamp the conduit cap 101. When the endoscope-side connector 41 is mounted on the conduit cap 101, a front end portion of the cylindrical portion 85 of the blade-equipped pipe body 64 is inserted into the conduit cap 101.

The endoscope 100 is placed at a predetermined position in the cleaning and disinfecting tank 4 in a state in which the endoscope-side connector 41 of the cleaning tube 40 is mounted on the conduit cap 101 of the endoscope 100 as described above, in this manner, the endoscope cleaning and disinfecting device 1 of the present embodiment cleans and disinfects the used endoscope 100 according to a predetermined program. Various steps of cleaning and disinfecting the endoscope 100 by the endoscope cleaning and disinfecting device 1 are substantially equal to conventional corresponding steps and hence, the detailed description of such steps is omitted.

in the various steps of cleaning and disinfecting, when a fluid W is supplied from a rear side toward a front side of the tube body 67, the tapered surface 81*b* of the valve element 63, the blade bodies 86 of the blade-equipped pipe body 64 and the like receive a pressure from the fluid W, thus generating a force for moving the valve element 63 toward the front side.

The valve element 63 is moved forward against the biasing force of the spring 62 by the forces generated by the tapered surface 81*b*, the blade bodies 86 and the like. The sealing body 82 is brought into close contact with a surface of the conduit cap 101 and with a periphery of the opening portion of the case body 71 of the connector case 61, so that the endoscope-side connector 41 is liquid-tightly connected to the conduit cap 101 (see FIG. 12). At this point of operation, the front end portion of the cylindrical portion 85 of the blade-equipped pipe body 64 is inserted into the conduit cap 101. With such a configuration, the fluid W flowing into the cylindrical portion 85 through the elongated holes 85*b* and the like is fed into the conduit cap 101 through the opening portion on a front side of the cylindrical portion 85, the hole portions 85*a* and the like.

Figure 13:
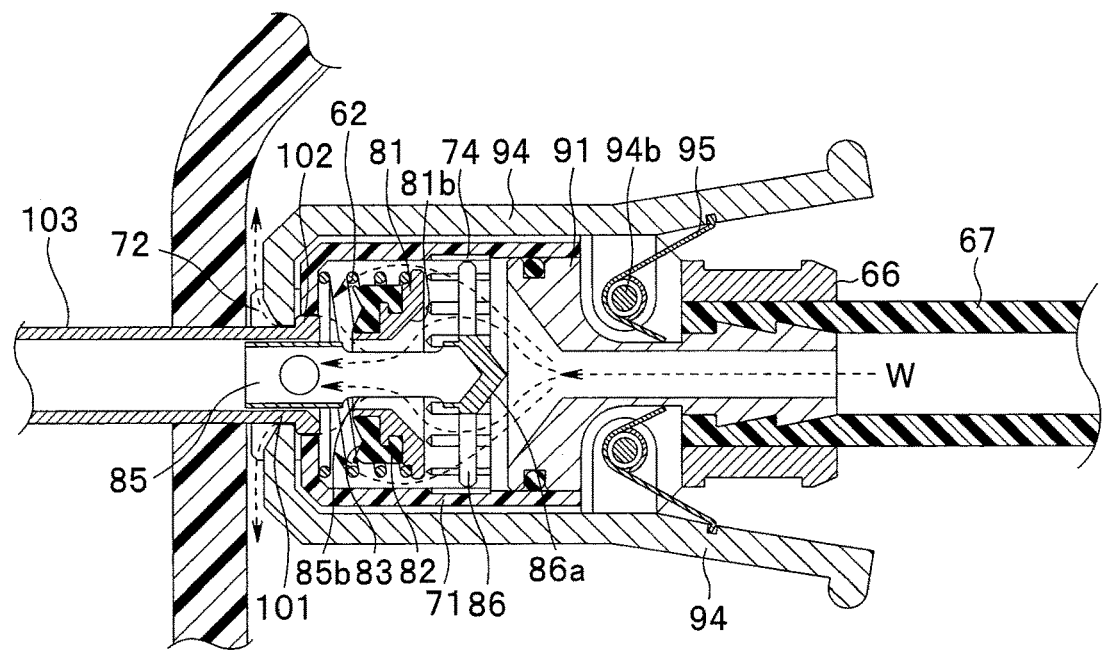
FIG. 13 is a cross-sectional view of the endoscope-side connector watertightly connected to the conduit cap, according to the first embodiment.

Until the endoscope-side connector 41 is liquid-tightly connected to the conduit cap 101, a portion of the fluid W supplied to the tube body 67 flows out through a gap formed between the conduit cap 101 and the opening portion 73 of the case body 71 of the connector case 61 (see FIG. 13). An outer surface portion and the like of the conduit cap 101 are also cleaned and disinfected with such fluid W flowing out through the gap.

In this case, at an initial stage after the start of the supply of the fluid W, the pressure of the fluid W supplied to the tube body 67 is reduced by the air chamber 44. In other words, the pressure of the fluid W, which is regulated to the regulator pressure by the regulator 17*b* (or the regulator 18*b*), is temporarily reduced to a pressure lower than the regulator pressure by a predetermined amount for a predetermined period in which air confined in the air chamber 44 is compressed to a predetermined volume.

During such a period in which the pressure of the fluid W is reduced in this manner, the valve element 63 stays at a half-opened position without achieving a sealing position where the sealing body 82 is brought into close contact with the surface of the conduit cap 101 and the periphery of the opening portion of the case body 71 of the connector case 61. Accordingly, the outer surface portion and the like of the conduit cap 101 are cleaned and disinfected with the fluid W of a sufficient flow rate.

In other words, each buffer unit 43 is interposed between the channel conduit 15 and the cleaning tube 40, which are disposed upstream of the endoscope-side connector 41. With such a configuration, compared with a case shown in FIG. 9 where the buffer unit 43 is not interposed (see broken line in FIG. 9), for example, it is possible to ensure a sufficient time period fir causing the fluid W to flow out to a vicinity of the conduit cap 101, and to ensure a sufficient flow rate of the fluid W caused to flow out (see solid line in FIG. 9). Accordingly, not only an inside of the channel of the endoscope 100, but also the outer surface portion and the like of the conduit cap 101 are precisely cleaned and disinfected.

According to such an embodiment, the liquid feeding conduit is configured to include the tube body 67 of the cleaning tube 40 through which a fluid flows, the endoscope-side connector 41 provided at one end of the tube body 67, the endoscope-side connector 41 being connected to the conduit cap 101 of the endoscope conduit 103, the valve element 63 provided in the endoscope-side connector 41, the valve element 63 being configured to move toward a side of the conduit cap 101 by a supply pressure of the fluid to thereby watertightly connect the endoscope-side connector 41 and the conduit cap 101, the spring 62 configured to bias the valve element 63 toward an opposite side of the conduit cap 101, and the buffer unit 43 configured to delay the movement of the valve element 63 toward the side of the conduit cap 101. Accordingly, not only the inside of the endoscope conduit 103 of the endoscope 100, but also the conduit cap 101 can be precisely cleaned and disinfected with the simple configuration.

In other words, by interposing the buffer unit 43 in the liquid feeding conduit, the pressure of a fluid supplied to the endoscope-side connector 41 can be temporarily regulated to a pressure lower than the regulator pressure. Accordingly, it is unnecessary to provide a pressure regulating mechanism, which regulates a fluid pressure to a pressure lower than the regulator pressure, to the channel conduit 15 or the like, and the fluid W of a sufficient flow rate can be caused to flow out to the vicinity of the conduit cap 101 with the simple configuration.

Further, a flow rate, an outflow time period and the like of the fluid W caused to flow out to the vicinity of the conduit cap 101 can be easily changed by merely tuning a capacity of the air chamber 44 in advance and hence, the conduit cap 101 can be precisely cleaned without requiring electronic control or the like of the pressure regulating mechanism.

In addition to the above, the flowing out of the fluid W to the vicinity of the conduit cap 101 can be achieved without changing the biasing force of the spring 62 and hence, it is unnecessary to reduce the biasing force of the spring 62 more than necessary. Accordingly, even in a case where the biasing force of the spring 62 reduces due to deterioration over time or the like, it is possible to ensure that a connection portion between the conduit cap 101 and the endoscope-side connector 41 has sealability which can be obtained when the fluid W art the regulator pressure is supplied.

Figure 14:
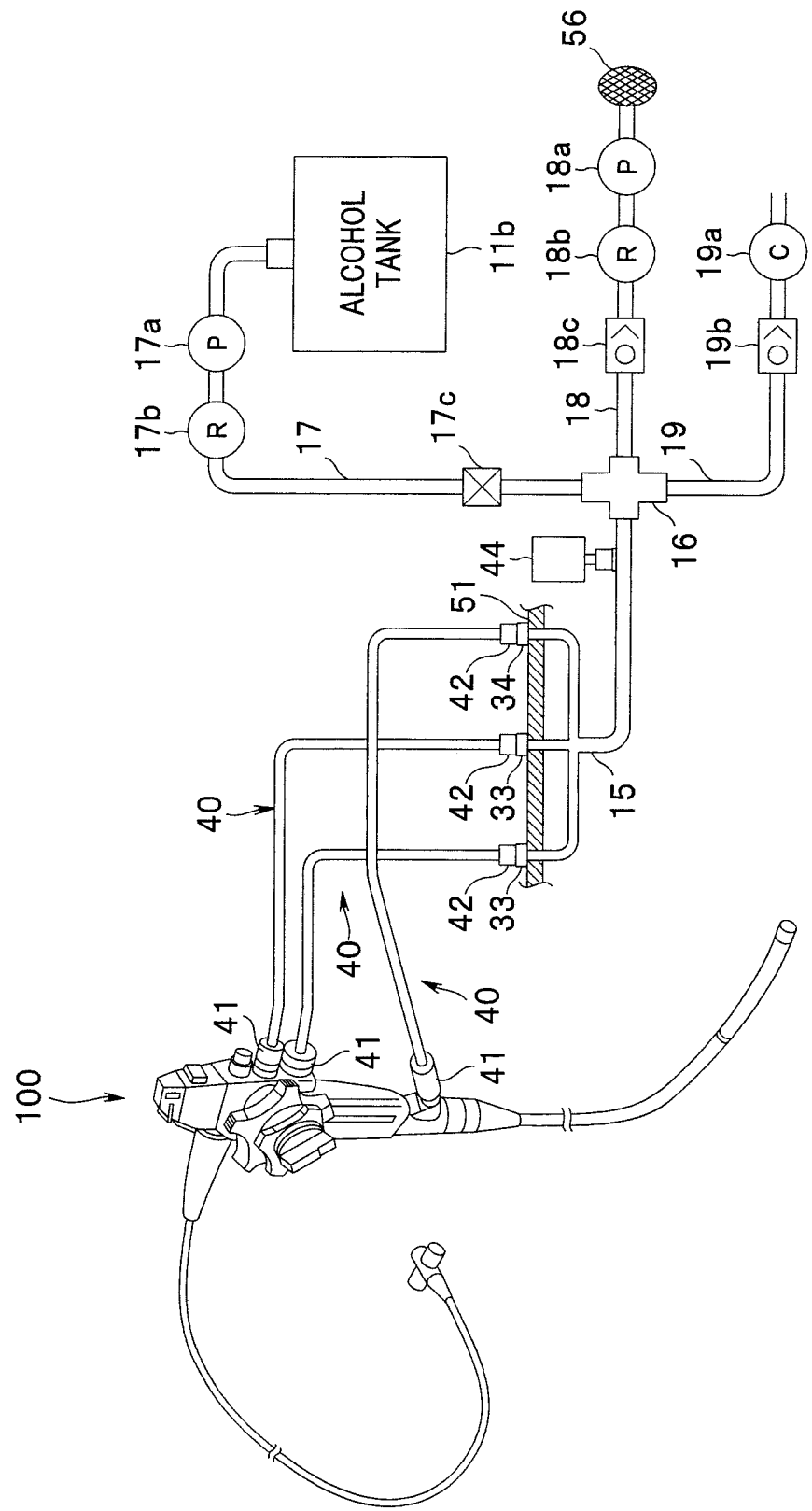
FIG. 14 is a schematic view showing a liquid feeding conduit connected to the endoscope, according to a modification of the first embodiment.

In the present embodiment, as shown in FIG. 14, for example, the air chamber 44 forming the buffer mechanism may be caused to communicate with an intermediate portion or the like of the channel conduit 15 with the opening portion directed downward. In such a case, the device-side connector 42 of the cleaning tube 40 is directly connected to the air feeding water feeding/forceps port 33 (or the forceps raising port 34) without interposing the buffer unit 43.

Next, a second embodiment of the present invention will be described with reference to FIG. 15 and FIG. 16. In the above-mentioned first embodiment, the buffer mechanism is formed using the air chamber. The present embodiment mainly differs from the first embodiment with respect to a point that the buffer mechanism is directly formed on the tube body 67 of the cleaning tube 40. Other components substantially equal to the corresponding components in the above-mentioned first embodiment are given the same reference symbols, and the repeated description will be omitted when appropriate.

Figure 15:
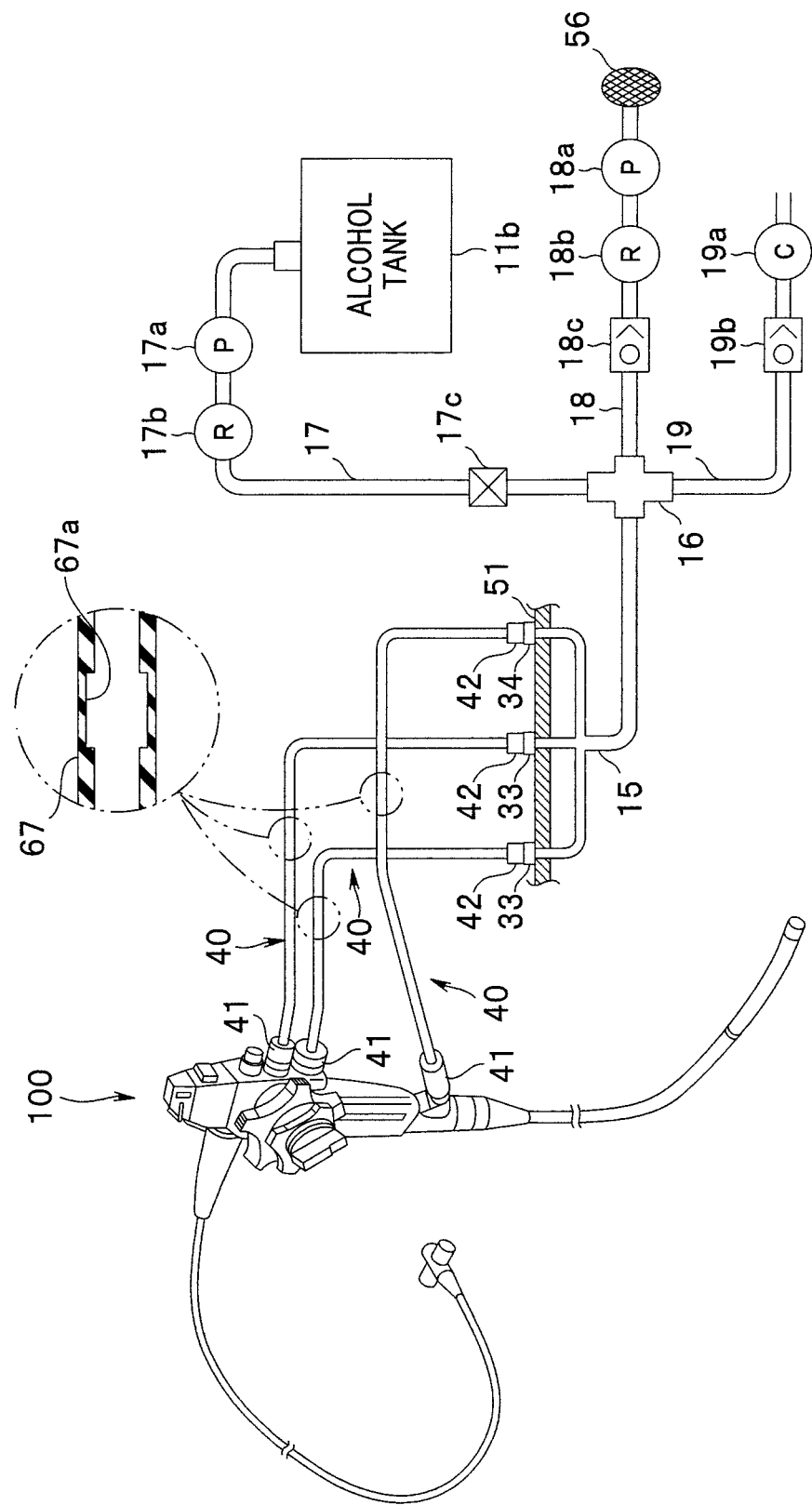
FIG. 15 is a schematic view showing a liquid feeding conduit connected to the endoscope, according to a second embodiment.
Figure 16:
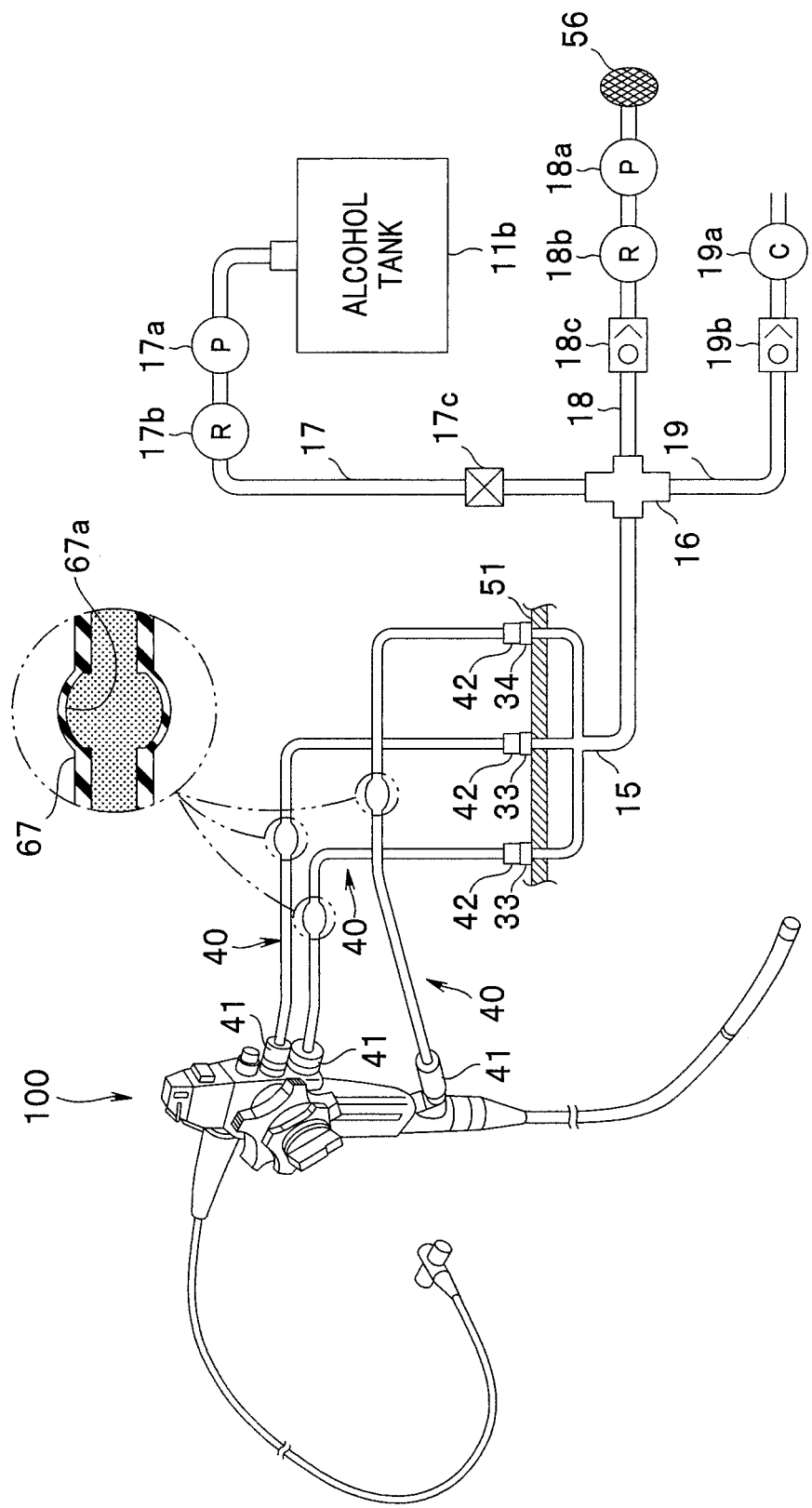
FIG. 16 is a schematic view showing the liquid feeding conduit at a time of supplying a fluid to the conduit cap, according to the second embodiment.

As shown in FIG. 15, in the cleaning tube 40 in the present embodiment, a thin wall portion 67a serving as the buffer mechanism is formed at part of an intermediate portion of the tube body 67.

The thin wall portion 67a is a portion for allowing a portion of the tube body 67 to be elastically deformed. In other words, the thin wall portion 67a can expand to a predetermined capacity due to elastic deformation when a fluid pressure equal to or greater than a predetermined value is applied to the tube body 67 (see FIG. 16).

With such a configuration, at the initial stage after the start of the supply of the fluid W, the pressure of the fluid W supplied to the tube body 67 is reduced by the thin wall portion 67a. In other words, the pressure of the fluid W, which is regulated to the regulator pressure by the regulator 17b (or the regulator 18b), is temporarily reduced to a pressure lower than the regulator pressure by a predetermined amount for a predetermined period in which the thin wall portion 67a is expanded to a predetermined capacity. With such a configuration, the present embodiment can also obtain the advantageous effects substantially equal to the advantageous effects of the above-mentioned first embodiment.

Next, a third embodiment of the present invention will be described with reference to FIG. 17 and FIG. 18. In the above-mentioned first and second embodiments, the liquid pressure of a fluid is temporarily reduced to delay the movement of the valve element 63. The present embodiment mainly differs from the above-mentioned first and second embodiments with respect to a point that a resistance is provided in the endoscope-side connector 41 to delay the movement of the valve element 63. Other components substantially equal to the corresponding components in the above-mentioned first embodiment are given the same reference symbols, and the repeated description will be omitted when appropriate.

Figure 17:
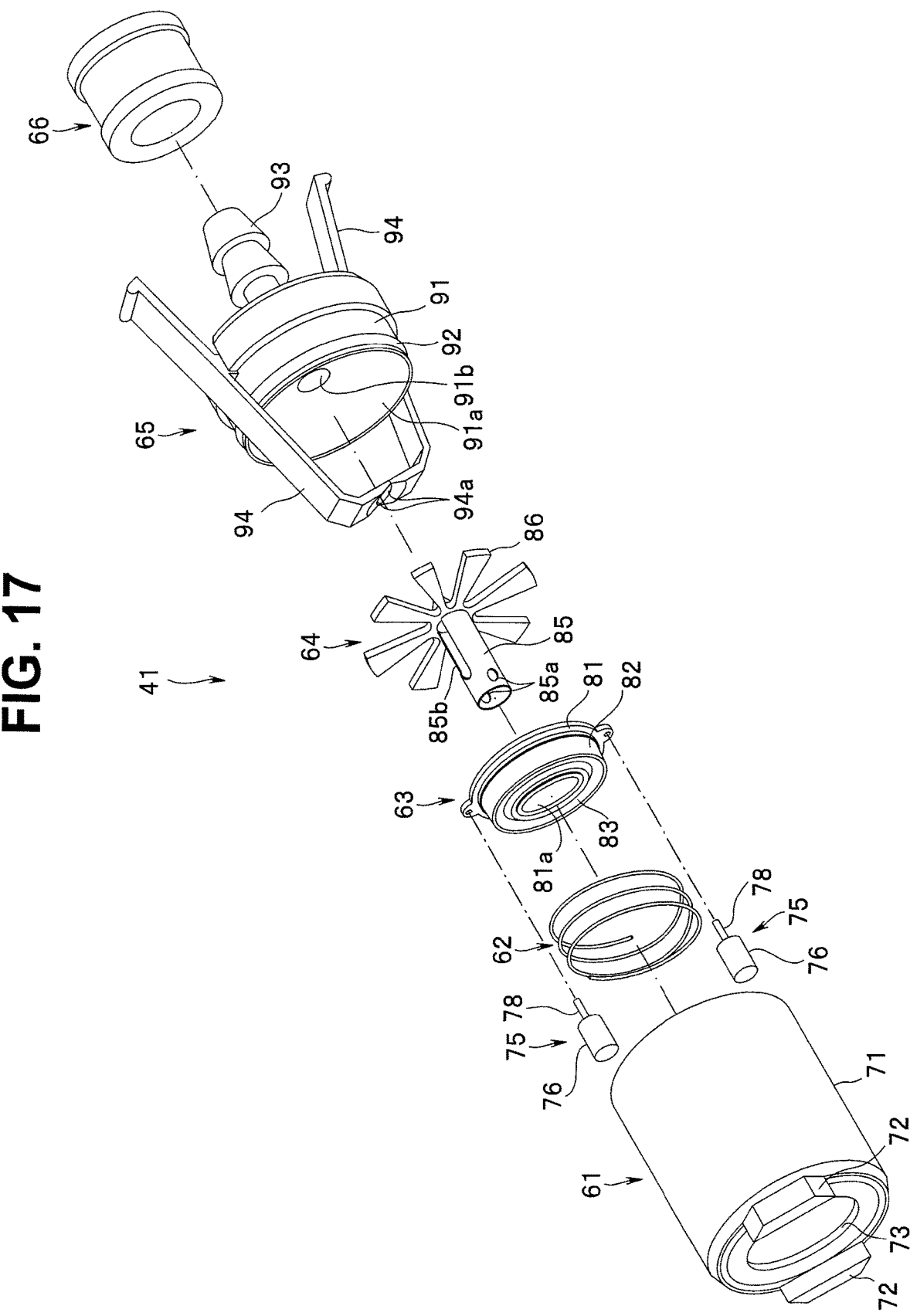
FIG. 17 is an exploded perspective view showing an endoscope-side connector of a cleaning tube according to a third embodiment.
Figure 18:
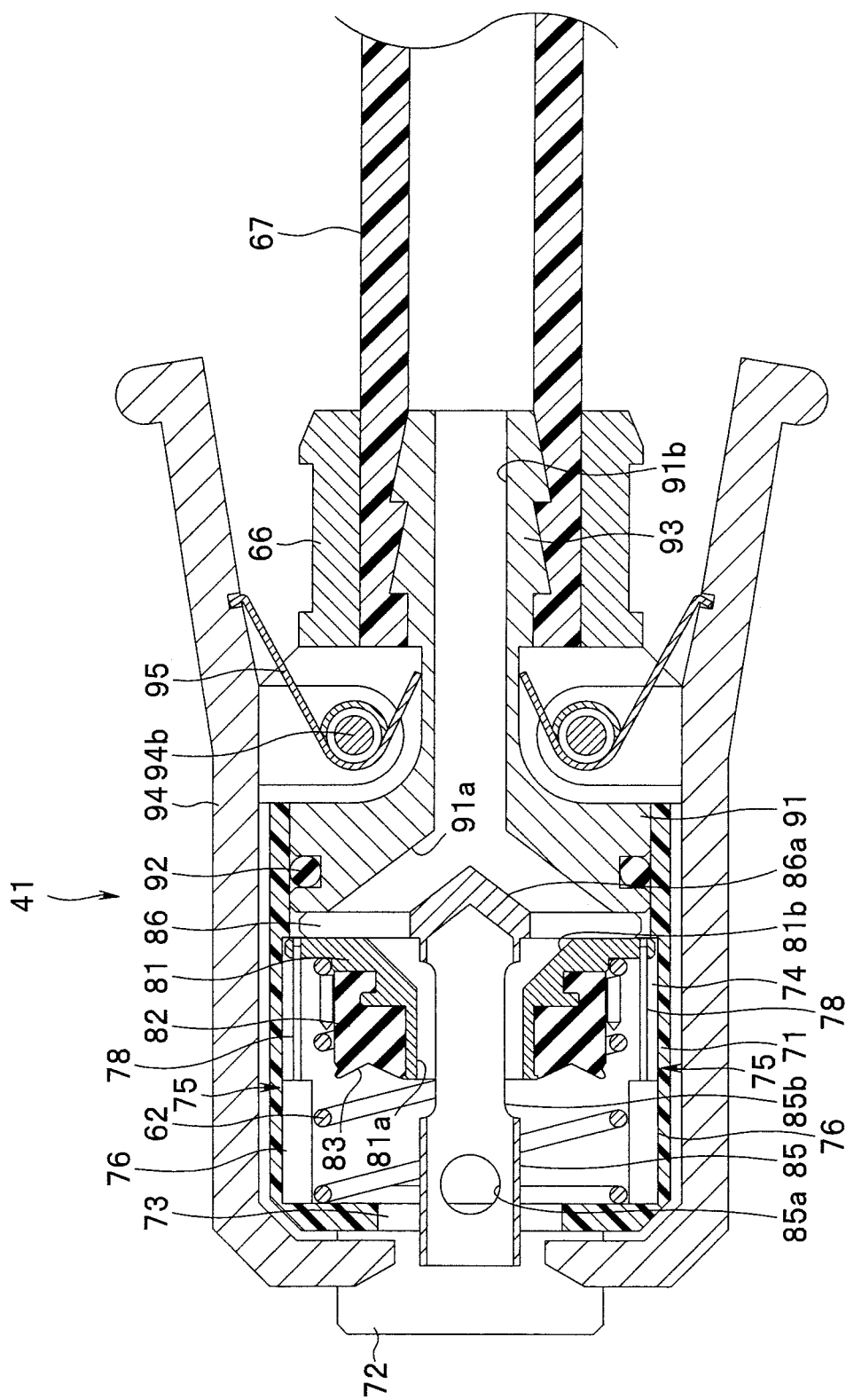
FIG. 18 is a cross-sectional view showing the endoscope-side connector of the cleaning tube, according to the third embodiment.

As shown in FIG. 17 and FIG. 18, dampers 75 serving as a buffer mechanism are provided in the endoscope-side connector 41. The dampers 75 are resistances provided for delaying the movement of the valve element 63, and are interposed between the distal end portion of the case body 71 and the valve element 63.

Figure 19:
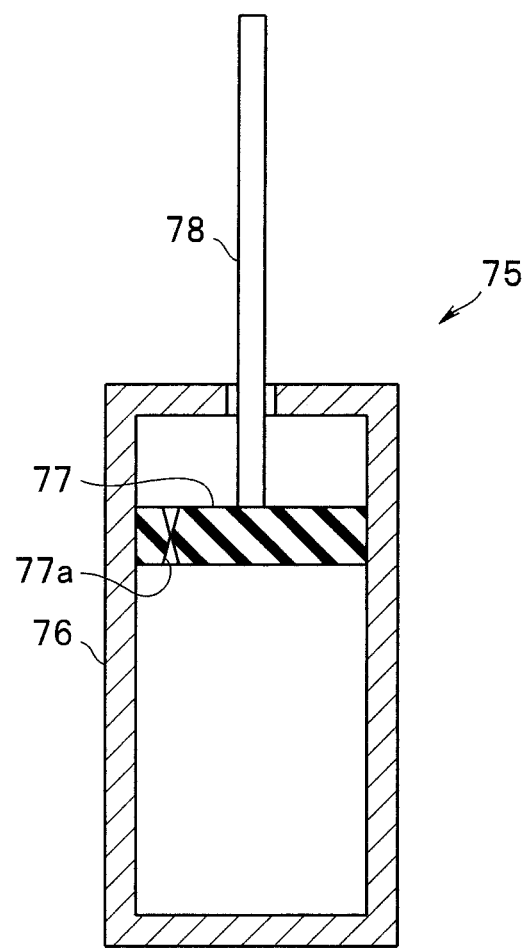
FIG. 19 is a cross-sectional view showing a damper according to the third embodiment.

As shown in FIG. 18 and FIG. 19, each damper 75 has a cylinder 76 fixed to the case body 71. The cylinder 76 is formed of a cylindrical body having a substantially cylindrical shape and having one closed end, for example.

A piston 77 having a substantially disk shape is slidably accommodated in the cylinder 76. The piston 77 has a leak hole 77a, being an orifice or the like, that communicates the inside and the outside of the cylinder 76 with each other.

One end side of a piston rod 78 is connected to the piston 77. The other end side of the piston rod 78 is coupled to the annular portion 81 forming the valve element 63.

In such a configuration, at the initial stage after the start of the supply of the fluid W, the valve element 63 starts the movement toward a side of the distal end of the case body 71 (toward the side of the conduit cap 101) by the pressure of the fluid W (regulator pressure) supplied to the tube body 67. At this point of operation, the damper 75 contracts while gradually discharging the fluid in the cylinder 76 through the leak hole 77a. The contraction of the damper 75 acts as a resistance against the movement of the valve element 63 and hence, the movement of the valve element 63 toward a side of the conduit cap 101 delays.

When the supply of the fluid W is stopped, the valve element 63 moves toward a side of the proximal end of the case body 71 by the biasing force of the spring 62. At this point of operation, the damper 75 expands while taking the fluid into the cylinder 76 through the leak hole 77a.

According to such an embodiment, the advantageous effects of the above-mentioned first and second embodiments can be obtained and, in addition to the above, a fluid pressure is not reduced also when the valve element 63 is moved. Accordingly, the fluid W can be caused to forcefully flow out to the vicinity of the conduit cap 101 and hence, it is possible to obtain an advantageous effect of more effectively cleaning and disinfecting the conduit cap 101 and the like.

Figure 20:
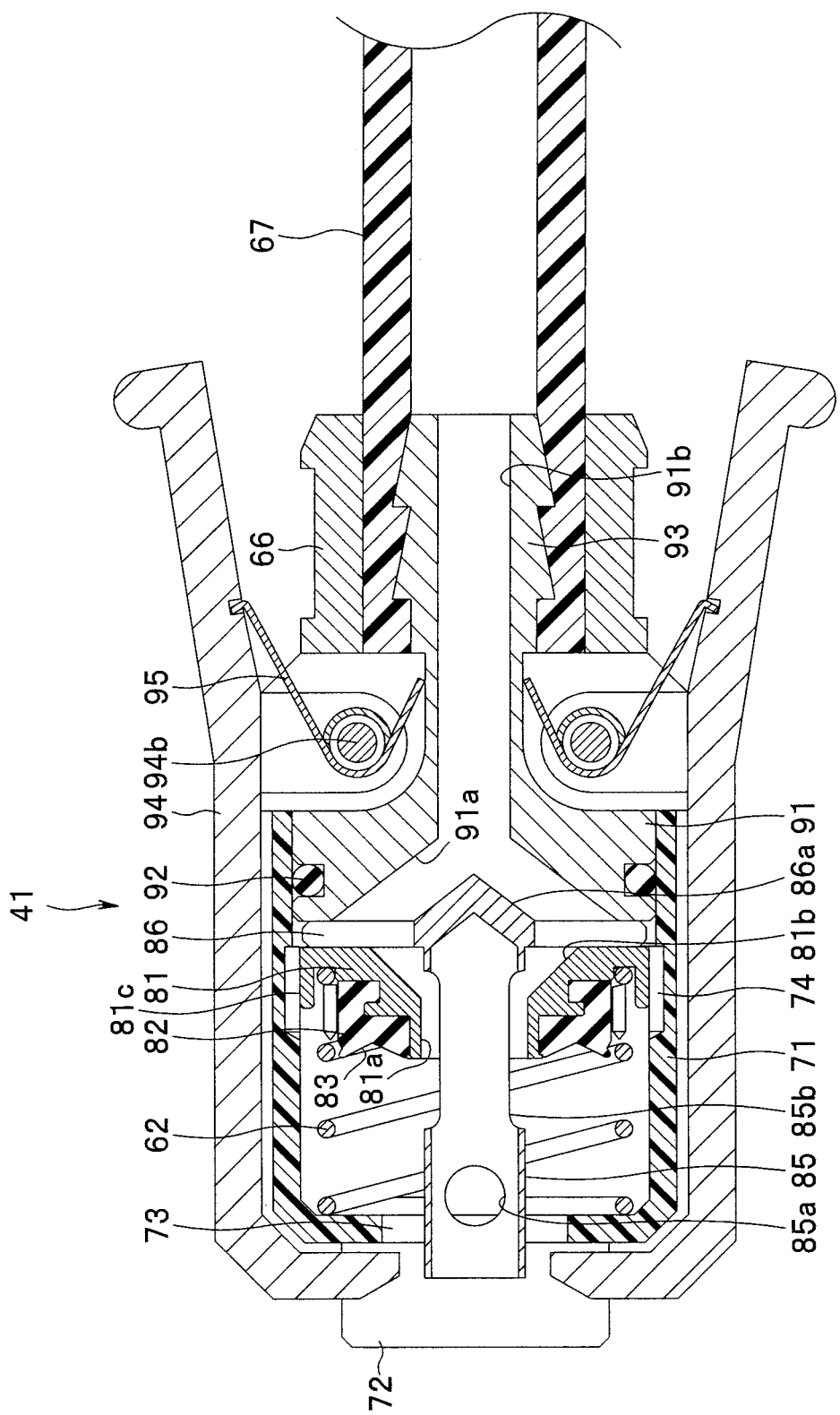
FIG. 20 is a cross-sectional view showing an endoscope-side connector of a cleaning tube, according to a modification of the third embodiment.

In the present embodiment, as shown in FIG. 20, for example, a sliding member 81c which is slidable against the case body 71 may also be provided in the endoscope-side connector 41 as a buffer mechanism. The sliding member 81c is, for example, a resistance provided for delaying the movement of the valve element 63, and is integrally formed with the annular portion 81 of the valve element 63. The sliding member 81c causes a sliding resistance between the sliding member 81c and the case body 71, thus delaying the movement of the valve element 63.

The present invention is not limited to the above-described respective embodiments, and various modifications and changes are conceivable. Such modifications and changes also fall within the technical scope of the present invention. For example, needless to say, the configurations of the above-mentioned respective embodiments and the respective modifications may be suitably combined.

What is claimed is:

1. A liquid feeding conduit that supplies a fluid to an endoscope conduit of an endoscope disposed in an endoscope reprocessor, the liquid feeding conduit comprising:
   a tube body through which the fluid passes;
   a connector provided at an end of the tube body, the connector being configured to be attached to and detached from a cap of the endoscope conduit;
   a valve provided in the connector, the valve being configured to move toward a side of the cap by a supply pressure of the fluid to thereby watertightly connect the connector and the cap;
   a biasing material configured to bias the valve toward an opposite side of the cap; and
   a buffer mechanism configured to delay the movement of the valve toward the side of the cap;
   wherein the buffer mechanism is a damper provided in the connector.

2. The liquid feeding conduit according to claim 1, wherein the damper comprises a plurality of dampers.

3. The liquid feeding conduit according to claim 1, wherein the damper includes a cylinder and a piston configured to slide in the cylinder.

4. The liquid feeding conduit according to claim 3, wherein the piston includes a leak hole through which a fluid flows.

5. The liquid feeding conduit according to claim 1, wherein the biasing material is a spring.

6. An endoscope reprocessor comprising:
   a liquid feeding conduit that supplies a fluid to an endoscope conduit of an endoscope, the liquid feeding conduit including:
      a tube body through which the fluid passes;
      a connector provided at an end of the tube body, the connector being configured to be attached to and detached from a cap of the endoscope conduit;
      a valve provided in the connector, the valve being configured to move toward a side of the cap by a supply pressure of the fluid to thereby watertightly connect the connector and the cap;
      a biasing material configured to bias the valve toward an opposite side of the cap; and
      a buffer mechanism configured to delay the movement of the valve toward the side of the cap;
   wherein the buffer mechanism is a damper provided in the connector.

7. The endoscope reprocessor according to claim 6, wherein the damper comprises a plurality of dampers.

8. The endoscope reprocessor according to claim 6, wherein the damper includes a cylinder and a piston configured to slide in the cylinder.

9. The endoscope reprocessor according to claim 8, wherein the piston includes a leak hole through which a fluid flows.

10. The endoscope reprocessor according to claim 6, wherein the biasing material is a spring.

11. A liquid feeding conduit that supplies a fluid to an endoscope conduit of an endoscope disposed in an endoscope reprocessor, the liquid feeding conduit comprising:
    a tube body through which the fluid passes;
    a connector provided at an end of the tube body, the connector being configured to be attached to and detached from a cap of the endoscope conduit;
    a valve provided in the connector, the valve being configured to move toward a side of the cap by a supply pressure of the fluid to thereby watertightly connect the connector and the cap;
    a biasing member configured to bias the valve toward an opposite side of the cap; and
    a buffer mechanism connected to the biasing member and configured to delay the movement of the biasing member toward the side of the cap.

* * * * *